United States Patent [19]

Hofmann et al.

[11] Patent Number: 5,057,421

[45] Date of Patent: * Oct. 15, 1991

[54] THIN FILM MEMBRANE ENZYME/COEMZYME REACTOR AND METHOD OF USING SAME

[75] Inventors: Frieder K. Hofmann, Oceanside; Wolfgang J. Wrasidlo, LaJolla, both of Calif.

[73] Assignee: Brunswick Corporation, Skokie, Ill.

[ * ] Notice: The portion of the term of this patent subsequent to Sep. 11, 2007 has been disclaimed.

[21] Appl. No.: 334,321

[22] Filed: Apr. 7, 1989

Related U.S. Application Data

[63] Continuation-in-part of Ser. No. 26,380, Mar. 16, 1987, Pat. No. 4,956,289.

[51] Int. Cl.$^5$ .................. C12N 11/02; C12N 11/08; C12N 11/14
[52] U.S. Cl. .................. 435/182; 435/180; 435/176; 435/177; 435/288; 435/817; 210/632
[58] Field of Search .............. 435/174, 180, 181, 182, 435/285, 286, 287, 288, 817, 176, 177; 210/632

[56] References Cited

U.S. PATENT DOCUMENTS 4,956,289 9/1990 Wrasidlo et al. ............... 435/180

Primary Examiner—David L. Lacey
Assistant Examiner—William K. Y. Chan
Attorney, Agent, or Firm—Waldron & Associates

[57] ABSTRACT

An enzyme reactor system is provided based on the entrapment of a coenzyme-requiring enzyme, a coenzyme, and a regeneration enzyme in a hydrogel layer coated on a support, and confined by an ultraporous thin film semipermeable membrane. The diffusion barrier confines the coenzyme-requiring enzyme, coenzyme, and regeneration enzyme but lets substrate and reaction products, exclusive of coenzyme, diffuse freely into and out of the hydrogel layer. In an alternate embodiment, the support is formed of an ultraporous thin film semipermeable membrane on a microporous or macroporous support, through which the reaction products, exclusive of coenzyme, can diffuse freely, but through which neither coenzyme-requiring enzyme, coenzyme, regeneration enzyme, nor substrate can pass. In this embodiment, the product is recovered in high purity, free of substrate, coenzyme-requiring enzyme, coenzyme, and regeneration enzyme. A constant supply of coenzyme for the enzyme reaction is assured by initially charging the hydrogel layer with an adequate supply of coenzyme. The problem of coenzyme depletion is solved by including a second enzyme in the hydrogel layer which regenerates the used coenzyme, thus recycling it. The substrates for both the primary and regeneration reactions are supplied in the circulating solvent. Reaction products, exclusive of coenzyme, are carried away by the solvent.

29 Claims, 2 Drawing Sheets

THIN FILM MEMBRANE ENZYME/COEMZYME REACTOR AND METHOD OF USING SAME

RELATED APPLICATION

This application is a continuation-in-part of our copending application Ser. No. 026,380, filed Mar. 16, 1987, now U.S. Pat. No. 4,956,289 entitled THIN FILM MEMBRANE ENZYME REACTOR AND METHOD OF MAKING AND USING SAME. U.S. Pat. No. 4,956,289 is incorporated herein by reference.

TECHNICAL FIELD

The technical field of the present application relates to thin film membrane enzyme coenzyme bioreactors. Specifically, this application relates to thin film membranes, preferably ultraporous, formed of cross linked polymer systems, and to methods and techniques for the utilization of such membranes for confining active enzymes and coenzymes as enzyme and coenzyme reactor structures, and the manufacture and use thereof.

BACKGROUND ART

Many biological reactions which are potentially interesting for large scale in vitro industrial use are prohibitively expensive due to the requirement for costly coenzymes. The present invention describes an application of the enzyme reactor described in copending Ser. No. 026,380 which will allow complex coenzyme-requiring enzymic reactions to be economically scaled up as industrial processes. The invention lies in the inclusion of coenzyme-requiring enzyme, coenzyme, and a coenzyme regeneration enzyme system within the hydrogel layer of the reactor such that the coenzyme will not diffuse out or be depleted.

A constant supply of coenzyme for the enzyme reaction is assured by initially charging the hydrogel layer with an adequate supply of coenzyme. In operation of the enzymatic process, the coenzyme is prevented from diffusing out of the hydrogel either by a thin film polymer membrane which is impermeable to the coenzyme or by switching to a solvent in which the coenzyme is not soluble to carry substrate materials. The problem of coenzyme depletion is solved by including a second enzyme in the hydrogel layer which regenerates the used coenzyme, thus recycling it. The substrates for both the primary (coenzyme-requiring) and regeneration reactions are supplied in the circulating solvent. Reaction products from the reaction of substrate and the coenzyme-requiring enzyme are carried away by the solvent, from which they may be recovered. The coenzyme produced from the reaction of substrate and the regeneration enzyme remains within the hydrogel layer while any other reaction products from that reaction are carried away by the solvent.

Most common, industrial, enzymatic reactions are carried out in bulk reaction systems, ordinarily in batch reactions. The enzyme component which catalyzes the desired reaction is usually discarded as waste at the conclusion of the reaction. This occurs even though the enzyme functions as a catalyst and theoretically it is therefore possible to recover and recycle the enzyme at the conclusion of the reaction. Apart from the expense of recovery, it has often been found that the activity of recovered and recycled enzymes is degraded by the recovery procedures and in many cases undesirable or intolerable contaminants are introduced.

For many enzyme catalyzed processes, the desirability and need for continuous, as opposed to batch, processing and other features has led to extensive investigations of techniques and means for the immobilization of enzymes on supports of one kind or another. The most commonly employed procedure at present is glutaraldehyde immobilization by the formation of covalent bonds to the enzyme, which form the basis for cross-linking the product to a physical support. The support is most often a granular solid, although there have been numerous investigations and use of other forms of supports, including membrane supports, particularly to physically entrap enzymes within the pores of membrane structures, most often with the additional use of chemical immobilization. It has been observed, however, that in many systems enzyme activity is impaired or even completely lost as a consequence of interference of the covalent cross-linking with the reactive site of the enzyme. There have been observations which reveal that the temperature and pH optima are also altered by such procedures. In some circumstances, advantage may be taken of the changes in properties, but on the whole, it is desirable to provide a technique which retains the original properties of the enzyme to the greatest possible degree.

In other contexts, there have been investigations of systems for physical entrapment or encapsulation of enzymes. The objectives of these procedures have generally been to avoid the unfavorable consequences of covalent bonding immobilization procedures, while retaining the advantages thereof. These systems and approaches have met with limited success and acceptance for a variety of reasons. Among these are characteristics which result in the loss of direct and intimate contact between the enzyme and the substrate, because of the limited diffusion capacities of such materials and structures, with the attendant losses in production rate and efficiency, and the rather substantial cost penalties involved.

One approach to physical entrapment of enzymes has been to confine the material on or in a membrane structure, where the enzyme remains lodged while the substrate is flowed through the membrane. The resulting stream is processed to recover the product, and the substrate is recycled. By these techniques, the art has attempted to provide direct and intimate contact between the enzyme and the substrate, and by using commercially available membranes, the costs of this type of immobilization are kept to a reasonable level. These techniques have not met with acceptance, however, since the efficiencies of the system may be impaired in other ways. Notably, there is a trade-off between the permeability of the membrane, i.e., the resistance to flow of the substrate process stream, and the effectiveness of the containment of the enzyme. When the controlling or limiting pore size of the membrane is optimal for confining the enzyme, the hydraulic resistance to flow of the substrate containing stream is often unacceptably high. When the pore size is enlarged to a level more consistent with the flow rates required for reasonable through-put, there is an increasing risk of enzyme loss into the product stream. In some circumstances, the result is an inconvenient burden on the product purification, but in other circumstances, such results are intolerable.

Most enzyme reactions in biological systems are very efficient in terms of the energy and substrates consumed, primarily because of their specificity. Efficiency is essential for competitiveness with other organisms. Enzymes are complex macromolecules which are "expensive" for the organism to manufacture. The energy investment in the enzyme is justified because in its lifetime it can catalyze millions of reactions, each at a low energy expense, and generally produce products which would be impossible to create in a living environment without catalysis.

The activity of some enzymes are dependent only on their structure as proteins, while others also require one or more nonprotein components, called cofactors. Cofactors may be metal ions or organic molecules called coenzymes.

A coenzyme is a molecule which is essential for, but consumed in the catalyzed reaction. Like the enzyme, coenzymes are valuable molecules which are preferably conserved. Coenzymes are organic molecules and generally contain as part of their structure one or another of the vitamins, which are trace organic substances which are vital to the function of all cells. Nearly all of the water-soluble vitamins, including all of the "B" vitamins, biotin and lipoic acid, function as components of coenzymes.

Coenzymes for the most part serve as intermediate carriers of functional groups, specific atoms or electrons which are transferred in the overall enzymatic reaction. For example, some coenzymes transiently bind functional groups in the enzymatic transfer from one molecule to another, e.g., thiamin pyrophosphate which transfers aldehyde groups and the pyridoxine coenzymes which transfer amino groups. Other coenzymes frequently provide reducing or oxidizing power for the enzyme to use in the reaction, e.g., pyridine nucleotides, flavin nucleotides. Examples of some of the principal coenzymes and the types of enzymatic reactions with which they involved are shown in the following table, TABLE I:

TABLE I

| Coenzyme | Entity transferred |
| --- | --- |
| Nicotinamide adenine dinucleotide | Hydrogen atoms (electrons) |
| Nicotinamide adenine dinucleotide phosphate | Hydrogen atoms (electrons) |
| Flavin mononucleotide | Hydrogen atoms (electrons) |
| Flavin adenine dinucleotide | Hydrogen atoms (electrons) |
| Coenzyme Q | Hydrogen atoms (electrons) |
| Thiamin pyrophosphate | Aldehydes |
| Coenzyme A | Acyl groups |
| Lipoamide | Acyl groups |
| Coenzyme $B_{12}$ | 1, 2 shift of hydrogen atoms |
| Biocytin | Carbon dioxide |
| Pyridoxal phosphate | Amino groups |
| Tetrahydrofolate coenzymes | One-carbon group transfer |

When the coenzyme is very tightly bound to the enzyme molecule, it is usually called a prosthetic group, e.g., the flavin nucleotides (containing riboflavin or $B_2$), coenzyme A (containing pantothenic acid), or the biocytin group of acetyl CoA carboxylase. In other cases, the coenzyme is loosely bound to the enzyme and essentially functions as one of the specific substrates for the particular enzyme, e.g., the pyridine nucleotides (containing niacin) and tetrahydrofolate (from folic acid).

In biological systems, every enzyme reaction which consumes coenzyme is linked to a reaction which generates coenzyme. If the coenzyme is tightly or covalently bound, these linked reactions, namely the enzyme reaction and the coenzyme regeneration reaction, take place on the same enzyme. If the coenzyme is loosely bound and functions as a substrate, then the linked reactions will take place on different enzymes. The linked reactions can either both produce needed products or a waste product may be generated.

Many enzymatic reactions which are dependent on cofactors, especially coenzymes, are of potential interest for large scale in vitro commercial and industrial use. Such use, however, is prohibitively expensive and costly, especially when loosely bound coenzymes are an essential component of the catalytic system. The necessary concentrations of these coenzymes along with the reaction substrates cannot be economically provided for in a large commercial scale. Accordingly, the present invention is directed to a method which would allow economical industrial use of enzymes which are coenzyme dependent, and involves the isolation of the coenzyme and the enzyme within the hydrogel layer, and the inclusion of a coenzyme regeneration system.

DISCLOSURE OF INVENTION

The structural options of the enzyme reactor for the present invention are the same as those disclosed in U.S. Pat. No. 4,956,289, described previously. In the simplest form the reactor consists of a hydrogel sandwiched between an impermeable surface and a hydrophilic thin film. The present application for complex reactions requiring a regeneration system for a coenzyme, is characterized by incorporating both the primary enzyme and the regeneration enzyme within the hydrogel layer before applying the thin film.

Coenzyme-requiring enzymes and coenzyme-regenerating enzymes are applied to a support surface in the form of a hydrogel, which is in turn covered with a thin film polymer membrane having a high porosity for the reaction substrate and water, and for the reaction product, but which is impermeable to the enzymes. The thin film membrane will most often have a pore size in the ultraporous range, i.e. from about 0.0005 to 0.1 microns, consistent with the dimensions of substrate molecules to be reacted and the product molecules produced. Such membranes desirably have high permeability to water, but will not pass large molecules, such as the enzyme.

After the thin film polymer membrane is in place, the reactor is charged with coenzyme by diffusion from an aqueous solvent. After the reactor is charged with coenzyme, the solvent system is changed to an organic solvent, e.g. hexane, in order to prevent the loss of the coenzyme by diffusion. In this situation, it may be necessary to periodically rehydrate the hydrogel by passing water over the thin film polymer membrane. If necessary, coenzyme can be added to replace any which is lost during rehydration of the hydrogel.

Alternatively, if the coenzyme is much larger than the substrate or product molecules, it can be added to the support surface with the coenzyme-requiring and regeneration enzymes in the form of a hydrogel. The thin film polymer membrane can then be applied which will be impermeable to both the enzymes and the coenzyme. Any desired solvents both aqueous and organic can then be used without fearing loss of enzymes or coenzyme.

Substrates for the two enzymes, the primary, coenzyme-requiring enzyme and the coenzyme regeneration enzyme are supplied by the organic or aqueous solvent. The concentration of substrate for the coenzyme-requiring enzyme to produce the desired product is reasonably high so as to favor the reaction but not waste substrate. The substrate for the coenzyme regeneration reaction is supplied at very high concentrations to facilitate a continuous supply of the coenzyme and to prevent reconversion of the reaction product from the reaction of substrate and coenzyme-requiring enzyme to substrate. The desired product and the product from the reaction of substrate with regeneration enzyme, exclusive of coenzyme, will be carried away by the appropriate organic or aqueous solvent and collected for recovery. The flow rate of the solvent and the substrate concentrations are balanced and manipulated so as to allow maximum production of the desired product while minimizing costs.

MODES OF CARRYING OUT THE INVENTION

Figure 1:
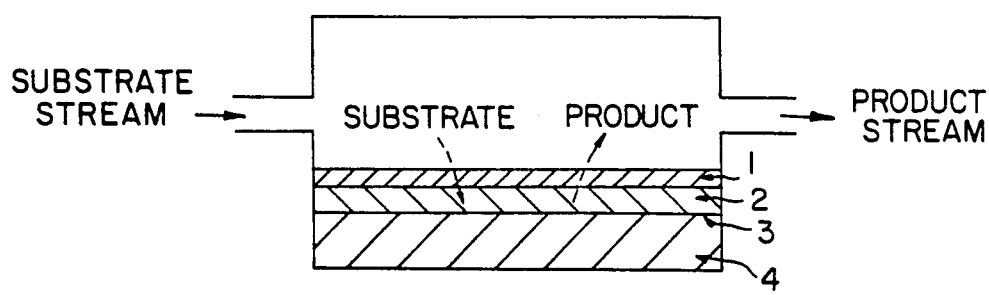
FIG. 1 shows a schematic reaction flow diagram, showing the operation of the present invention in its simplest embodiment and the simplest composite structure of the ultraporous thin film membrane enzyme reactor of the present invention.

For many enzyme catalyzed reactions, the limitations of bulk reaction systems are not a problem, since many inexpensive enzymes are available that do not warrant concern over such limitations. In other contexts, however, there has been considerable interest and effort devoted to the development of effective immobilized enzymes. The objectives of such efforts are often the extension of the functional life of the enzyme, ease of separation and reuse of the enzyme, greater stability over a wider range of operating conditions, the avoidance of contamination of products, the capacity for continuous production, and improved purification of reaction products.

The immobilization techniques most frequently employed to achieve these objectives generally alter the activity, stability, specificity, reaction rates, or other properties of the enzyme, most often in an undesirable way. The procedures which avoid one set of difficulties have generally resulted in a different set of problems. Such procedures often reduce reaction productivity and add processing complexity and expense, as well as other difficulties, as is well known.

In the present invention, then, there is provided an enzyme reaction system which overcomes the major problems of bulk reaction systems without the introduction of the significant disadvantages of the prior art approaches to the problems.

In the present system, the enzyme is not required to be chemically or physically altered in any way, and retains its full desirable range of properties, particularly activity, specificity, and optimum operating conditions. The substrate and product are readily separated from the enzyme, so that there are no problems of product contamination with the enzyme. Neither product nor feed stream impurities accumulate beyond trivial levels, so that the active life of the enzyme is extended and surprisingly protracted, with no initial or gradual compromise in any of the properties. The reaction rates are high and do not materially decline over time. By use of some of the optional features of the present system, many reactions can be performed in a fashion that permits the continuous and substantially complete recovery of the reaction product in high purity and concentration in an effluent stream independent of the substrate feed, permitting highly economical and efficient product recovery virtually totally free of contamination by the enzyme, the substrate, and by impurities in the substrate feed. The reaction product can be recovered in most cases in sterile form, if desired, without sterilization of the substrate feed. The reactions can be performed in continuous process, with high feed throughput and high productivity, and by virtue of the specific nature of the reaction system can be implemented with simple and inexpensive equipment on virtually any scale of production required. In addition, the system is readily amenable to automation, and offers low labor and skill requirements in set up, initiation, operation, and maintenance. The system is adaptable to any enzyme and substantially any substrate, and is of general applicability. Operating conditions at the optimum for any specific enzyme-substrate combination can be readily accommodated.

Additionally, the enzymes are provided with the necessary coenzymes which are kept in close proximity to the enzymes and which facilitate the enzyme-substrate reaction. The substrate for the reaction needed to regenerate the coenzyme is supplied at a very high concentration to facilitate a continuous supply of coenzyme and to prevent the reconversion of the product to the primary substrate.

These and still other advantages and objectives are provided in the present invention by virtue of the employment of the enzyme in the form of a hydrogel confined on a surface by a porous, ordinarily ultraporous, thin film semipermeable membrane. The substrate feed is passed over the thin film membrane surface, the substrate enters the reaction zone defined by the enzyme gel by diffusion through the thin film semipermeable membrane, and the reaction product diffuses out of the reaction zone and is recovered. Because of the particular properties of the thin film semipermeable membrane, the diffusion is very rapid and production rates are high.

Reduced resistance to flow by diffusion through the membrane is probably the single most important feature of thin film membranes in the context of the present invention in comparison to the state of the art ultraporous membranes. The ability to closely control the pore sizes is of considerable import as well.

It has come as a considerable surprise and benefit that the ultraporous thin film membranes are exceptionally effective for molecular separations. While such procedures are sometimes performed with conventional ultraporous membranes, there is a rapid fouling and blockage of the membranes, ordinarily associated with plugging of the pores of the membrane structure which does not occur with the thin film ultraporous membranes. In the context of the present invention, advantage is taken of the effectiveness of the ultraporous thin film membranes to perform just such molecular separations.

An illustrative and schematic representation of the simplest embodiment of the ultraporous thin film membrane enzyme reactor of the present invention is shown in FIG. 1, wherein the thin film diffusion barrier 1 is shown supported on and confining enzyme gel layer 2, which in turn is supported on support 4, having surface 3.

In operation, substrates for both the coenzyme-requiring and the regeneration enzymes, in an aqueous solution, are passed along the thin film surface in a continuous flow stream. Since the concentration of substrates in the gel is initially zero, the concentration gradient causes diffusion of the substrate molecules through the thin film and into the enzyme hydrogel. Conditions are maintained at suitable values for the enzyme-substrate reactions to proceed, preferably at or near optimum conditions for the reaction. The enzyme hydrogel constitutes a reaction zone under these conditions, where the enzymes will act on the substrates to produce the products. As the reactions proceed, the concentration of the products in the enzyme hydrogel increases, and a concentration gradient for the products is established which drives the passage of the products, exclusive of coenzyme, out of the gel, through the thin film, and into the feed stream. The concentration of substrates in the feed stream is preferably kept at a level high enough to sustain a concentration gradient which will continue to drive the diffusion of substrates into the enzyme gel, and, if the process stream is recirculated in continuous fashion, the products are preferably removed to sustain an appropriate concentration gradient to drive diffusion of the products out of the enzyme gel. It will be readily apparent as well that the thin film semipermeable membrane preferably has a pore size large enough to relatively freely pass the substrate and product through under the force of the diffusion process, but small enough to prevent the enzymes and, if possible, the coenzyme from passing through the thin film semipermeable membrane. If the coenzyme is too close in size to the substrate or product molecules, the thin film membrane pore size cannot be used to prevent coenzyme from passing through the membrane. In this case, as discussed below, it is possible to vary the substrate and product solvent so that the coenzyme is insoluble in the solvent while the substrates and other products remain soluble.

In this simplest form of the invention, the support is not involved other than in the role of providing an adequate physical structure to hold the enzyme gel and the thin film. In that context the support can be virtually any material which is substantially inert to the enzyme reaction system. It is desirable that it afford a high surface area for the thin film diffusion barrier and the underlying enzyme hydrogel, and it may be particulate, fibrous, or in the form of a flat surface. The support may be made of metal, glass, coated paper, polymer materials, or the like.

Figure 2:
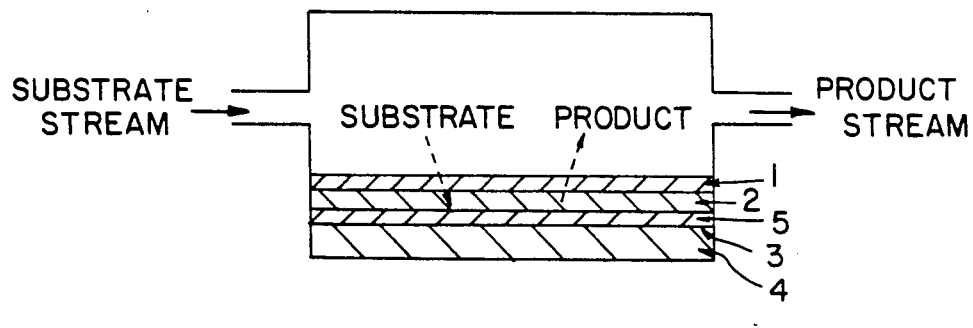
FIG. 2 shows the same schematic reaction flow diagram as FIG. 1, with a variation of the composite structure of the ultraporous thin film membrane enzyme reactor.

The simplest embodiment of the invention functions most efficiently if the support is dense or nonporous. If the support is nonporous, the product can only diffuse back into the feed stream which is preferred over allowing the product to diffuse into the support itself. It is possible, however, to utilize a porous support and still have the reactor function efficiently if the surface of the support is first coated with an impervious coating or dense thin film which essentially makes the support nonporous. Such a coated porous support can be seen in the embodiment shown in FIG. 2, which is a variation of FIG. 1, wherein the support 4 is porous, preferably microporous, and has interposed between its surface 3 and the enzyme hydrogel 2 a second thin film semipermeable membrane 5, which shall also be referred to as the support surface thin film membrane. As in the simplest embodiment of the invention, the thin film diffusion barrier 1 is supported on and confines enzyme hydrogel layer 2. In this embodiment, the support surface thin film membrane is a dense thin film which serves to make the porous support impervious to the enzyme, substrate, and product. Possible porous supports which would be useful in this embodiment are the same as those discussed below in connection with the alternative embodiment shown in FIG. 3. The other components of this embodiment are discussed herein in connection with the embodiment shown in FIG. 1.

The coenzyme-requiring enzyme, coenzyme, and regeneration enzyme are applied to the surface of the support as a hydrogel by deposition of a coating of appropriate thickness to the support surface. The aqueous enzyme/coenzyme coating forms a stable gel structure on the support surface.

The enzyme/coenzyme solution is deposited on the support, conveniently by dipping the support into a bath of the solution followed by spreading or draining or the like to remove excess, regulate thickness of the gel layer, and to assure a uniform, continuous coating on the support. Gel is formed by removal of water.

The gel layer is preferably no thicker than is necessary to achieve a stable, continuous and active layer. Excessive thickness is generally wasted, since it will be the components of the system nearest the thin film semipermeable membrane layer which will be the most active. It is preferable to add additional surface area to increase productivity. In light of these criteria, the enzyme hydrogel layer will ordinarily be in the range of from about 1 to about 10 microns in thickness. If thinner hydrogel layers are employed, it is difficult to maintain the continuity of the layer, and in thicker layers, the rate of diffusion to the distant regions is too slow to contribute materially to the productivity of the system.

As an optional variation, the enzyme hydrogel may be formed by dissolving the coenzyme-requiring enzyme, coenzyme, and regeneration enzyme in an aqueous solution of a hydrogel forming material, ordinarily a hydrogel forming polymer, followed by the application of a coating of the solution on the support, and then causing the solution to gel. Many such hydrogel materials are known to the art, and the present invention may be practiced with substantially any of the many natural and synthetic hydrogel forming polymers which meet a few simple and straightforward criteria.

The gel forming polymer is preferably chemically compatible with the enzyme reaction system, not susceptible to contamination of the product stream, capable of forming a stable gel which will include the enzyme and have a high porosity for water, substrate, and product. Preferably, the gel has a much higher porosity than the thin film diffusion barrier. When the system is used in connection with food or pharmaceutical applications, it is generally necessary that none of the constituents be toxic. Many hydrogel forming materials are generally recognized as safe in such applications. In addition, it is preferred that the gel be at least partially cross linked if possible, and still more preferably that it be irreversibly bound to the support and to the thin film semipermeable membrane.

The preferred hydrogel forming polymers for use in this optional embodiment of the present invention include gel forming hydrophilic polymers and copolymers of monomers containing carboxylic acid groups, hydroxyl groups, amine groups, alginic acid, guar gum, and the like.

The enzyme/coenzyme and polymer solution is deposited on the support, conveniently by dipping the support into a bath of the solution followed by spreading or draining or the like to remove excess, regulate thickness of the gel layer, and to assure a uniform, continuous coating on the support. The gel is formed by gellation in known manner. Light cross linking, where possible is conducted either before or, preferably, after gellation. The enzyme is physically entrapped and confined within the gel, but does not materially react with the polymer or any of the gel forming constituents.

The concentration of the coenzyme-requiring enzyme, coenzyme, and regeneration enzyme within the polymer gel is not a narrowly critical consideration, but as a general rule, if this variation is used, it is preferred that the concentration be as high as possible without interfering with or disrupting the physical or chemical integrity of the gel structure and its capacity to enhance the physical stability of the enzyme hydrogel layer. Most polymer gels will accommodate substantial proportions of the coenzyme-requiring enzyme, coenzyme, and regeneration enzyme, up to as much as ninety percent of the total solids of the gel. The coenzyme-requiring enzyme, coenzyme, and regeneration enzyme will ordinarily be included in an amount of from the slightest amount, sufficient to show enzymatic activity on the substrate, e.g. one percent, up to ninety percent of the solids content (dry weight) of the gel. Most often, the coenzyme-requiring enzyme, coenzyme, and regeneration enzyme will be from about forty to about eighty, and preferably from about fifty to about seventy, weight percent of the dry gel.

It will be readily apparent to those of ordinary skill that the reactive capacity of coenzyme-requiring enzyme, coenzyme, and regeneration enzyme is determined by its activity, and not in terms of weight percent. Since activity varies widely among enzymes, the reactive capacity will be dependent on the nature of the enzymes employed.

As in the simplest embodiment, the coenzyme-requiring enzyme, coenzyme, and regeneration enzyme and polymer hydrogel layer will ordinarily be in the range of from about 1 to about 10 microns in thickness.

As another optional variation, the coenzyme-requiring and regeneration enzymes may be applied to the support, with or without hydrogel forming polymer, as a hydrogel. Once the thin film membrane reactor is formed as discussed below, the reactor is charged with coenzyme by diffusion from aqueous solvent.

The thin film semipermeable membrane layer is applied directly on the surface of the hydrogel layer, and is preferably formed in situ by one or more of the techniques discussed in detail in the application of Wolfgang J. Wrasidlo, ULTRAFILTRATION THIN FILM MEMBRANES, U.S. Pat. No. 4,814,082, filed Oct. 20, 1986, and incorporated by reference herein, particularly for the disclosure to those of ordinary skill in the art of the full range of variables and parameters which determine the making of the thin film and the properties thereof, but also with regard to the support structure, and other parameters of import herein. Preferred among these is the application to the surface of a relatively dilute solution of polyethylene imine, by dipping or the like, followed by draining the coating until a golden color forms, in about two to five minutes, followed by contacting the surface of the solution with an immiscible solution of toluene diisocyanate, preferably in hexane. The TDI reacts to cross link the PEI only at the interfacial boundary of the immiscible phases, and thus forms a thin film. By controlling the extent of the cross linking reaction, the pore size of the thin film is determined.

The pore size of the thin film is preferably greater than the effective diameter of both the substrate molecule and the product molecule, so that both these components can diffuse relatively freely through the diffusion barrier. At the same time, the pore size is preferably less than the effective diameter of the enzymes or the coenzyme, whichever is smaller, so that they may not pass the barrier and remain entrapped in the hydrogel layer. This is assuming the coenzyme is larger than the substrate or product molecules. It is important to recall that effective diameters for purposes of the present invention are different for highly linear molecules than for generally spherical or globular molecules, and the pore sizes of the membrane are applicable to generally globular molecules such as those employed for the determination of molecular weight cut off values by which the pore sizes are inferred. It is a relatively simple matter to determine the effective molecular diameter for any enzyme, substrate or product by measuring retention on filtration membranes of varying pore sizes, preferably by diffusion but if necessary by filtration under pressure.

Functionally, the maximum useful pore size is the largest which will retain the enzymes and coenzyme without detectable losses. Any pore size much smaller than the maximum, increases flow resistance for the substrate and product diffusion is impeded. Thus, there is a disadvantage to a pore size any smaller than required.

The present system is not applicable to any enzyme substrate reaction where the effective molecular size of the substrate and/or the reaction product is greater than the enzyme, since any thin film semipermeable membrane having a pore size effective to contain the enzyme in the hydrogel reaction zone will not in that case permit the effectively larger molecule to diffuse into and/or out of the reaction zone. If the coenzyme is the same size as or smaller than the substrate or product molecules, the thin film semipermeable membrane preferably has a pore size which retains the enzymes without detectable losses. The coenzyme can be retained in the hydrogel layer in this situation by using solvents for the substrates and other products in which the coenzyme is insoluble.

Diffusion through the thin film semipermeable membranes in the present invention is ordinarily rapid, so that the reaction can proceed at effective rates. The speed of diffusion is a direct consequence of the very thin structure of the diffusion barrier, so that the thinnest possible thin film membrane layers are preferred in the present invention. The capacity of the thin film semipermeable membranes to pass the substrate and product molecules without substantial plugging or clogging of the membrane pores over time is critical to sustaining the high levels of diffusion on which success is dependent.

The polymer systems for use in the thin film semipermeable membrane of the present invention are all those cross linked polymer species employed in the formation of membranes. As those of ordinary skill in the art will recognize, the selection of polymer and cross linking systems will most often depend on the intended environment of use and the service duty required of the ultraporous thin film semipermeable membranes. A wide diversity of such materials and systems is known. See for example, Kesting, Robert E., *Synthetic Polymeric Membranes: A Structural Perspective*, 2d. Ed., Wiley-Interscience, New York, 1985. Only cross linked systems are a part of the present invention, but as that term is employed herein, it is intended to include those polymers formed from monomers which cause, at least in part, a high degree of branching to provide integral cross linking as a part of the polymer structure, particularly those formed in interfacial condensation polymerizations, as well as reactions of polymers with cross linking reagents which tie different polymer molecular chains together. Such polymers include, generally any crosslinkable member selected from the group consisting of polysaccharides, polysilicones, polycarbonates, polyamides, polyacrylics, polyimines, polyethers and polysulfones.

It will most often be preferred or necessary to employ polymers which are available in forms which are soluble in solvents, to facilitate the formation of thin films of the polymer solution and thereafter to cross link the polymers with a cross linking reactant at the interface with a separate phase in an interfacial reaction. Typical of this class of polymer systems is the preferred system in the present invention, an aqueous solution of polyethylene imine, which is then spread in a thin layer on the surface of a supporting medium, and thereafter contacted with a dilute solution of toluene diisocyanate in hexane to form polyurea cross links. This preferred polymer system is the basis of much of the discussion herein, and is sometimes referred to as the PEI/TDI polymer system.

Also of considerable interest is the polyamide resulting from cross linking of the PEI with isophthaloyl dichloride, sometimes referred to as the PEI/IPC polymer system.

Other polymer systems of interest are the fully aromatic polyamides formed by interfacial condensation polymerization from epiamine, m-phenylene diamine and other diamines and the like, condensed with IPC and/or TMC, and a variety of other related species. This system is typical of the formation of ultraporous thin film membranes from monomeric systems.

When the thin film semipermeable membrane is a polyelectrolyte, it may effect a pH optimum shift for the enzyme. Depending on the charge density, the shift can be as much as one pH unit. The direction of the shift is dependent on the polarity of the charge. This characteristic of the thin film semipermeable membrane provides an additional means to control the pH shift and pH optimum of the enzyme by choosing the appropriate charge polarity and charge density of the thin film polymer.

In use, the enzyme reactor structure defined by the composite of the ultraporous thin film semipermeable membrane, the intermediate enzyme hydrogel layer, and the support, will be incorporated into a physical containment reactor vessel for use. The vessel is preferably designed to accommodate a very large surface area, since it is the surface area which will be the primary determinant of the reactor production capacity. A variety of constructions are known to those of ordinary skill in the art, and it is possible to adapt any of them in self evident fashion to the requirements of the enzyme reactor of the present invention. It is preferred, when the support is not porous, to form the enzyme reactor either on a fibrous, e.g. glass fiber, support, or in other circumstances, on thin flat plates of films of supporting materials. In the case of fibrous supports, the reactor vessel is quite simple, requiring only a vessel with an inlet and outlet. As shown in FIG. 1, the fibrous enzyme reactor is packed inside the vessel, and the feed steam is pumped through the reaction vessel at an appropriate rate. The effluent stream is processed to recover the product, and the unreacted feed stock is preferably recycled.

In the case of thin plate forms, it is readily apparent the enzyme hydrogel and thin film semipermeable membrane are desirably applied to both faces of the plates, which are then mounted in a reactor vessel in a spaced array suitable to define flow paths for the feed-effluent stream to pass therebetween.

In either case, the control of the conditions of the reaction, by controlling the composition of the feed stream, the pH, temperature, and like enzymatic reaction determinants, are all well within the ordinary skill of the art. Likewise, the recovery of the product from the reaction vessel effluent stream is well known technology to those of ordinary skill. Neither of these aspects of the reaction forms any part of the present invention.

Figure 3:
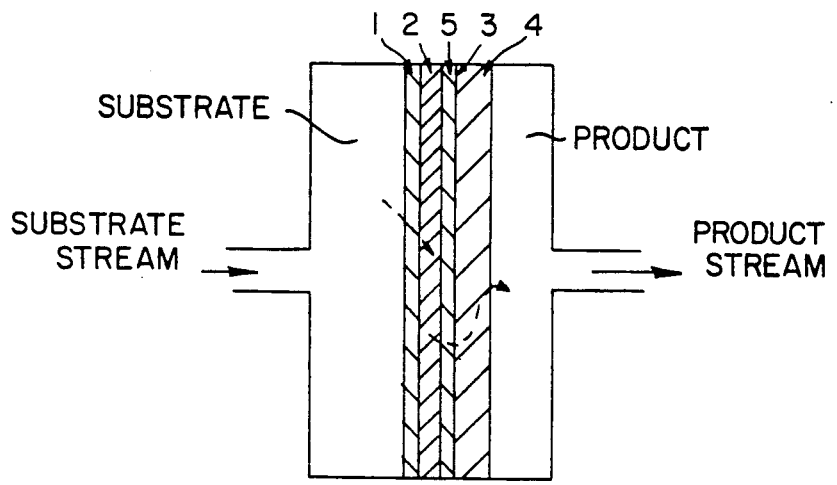
FIG. 3 shows a schematic reaction flow diagram, showing the operation of the invention in its flow through embodiment and another embodiment of the structure of the ultraporous thin film membrane enzyme reactor of the present invention.

In an alternative embodiment of the present invention, shown in FIG. 3, the support 4 is porous, preferably microporous, and has interposed between its surface 3 and the enzyme hydrogel 2 a second thin film semipermeable membrane 5, which shall also be referred to as the support surface thin film membrane. As in the simplest embodiment of the invention, the thin film diffusion barrier is supported on and confines enzyme hydrogel layer 2. In this alternative embodiment, particularly in enzyme reactions which result in a product molecule smaller than the substrate molecule, the pore sizes of the two thin film membrane components will be different, so that the substrate can diffuse through the thin film semipermeable membrane on the feed stream side, as shown in FIG. 3, but not through the support surface thin film membrane, while the smaller molecules of the reaction product can diffuse through both, but particularly through the support surface thin film membrane into a product stream where the product is recovered free of substrate, as shown in FIG. 3. In this case, the increment of product which initially diffuses into the feed stream is allowed to accumulate, so that the concentration reaches, over time, an equilibrium level in relation to the gel concentration, and diffusion into the feed stream then ceases, and the only concentration gradient will be with the product stream.

The support in this embodiment is necessarily porous, particularly microporous. Within limits, the support may be made of a wide diversity of materials. Preferred supports are those integral, skinned synthetic polymer microporous membranes, composed of a diversity of polymer materials, including polysulfones, polyether sulfones, polyvinyl chlorides, chlorinated polyvinyl chlorides, diverse polyamides, polyesters, polycarbonates, polyurethanes and polyureas, polysilicones, cellulose derivatives, and the like.

Particularly preferred are the polysulfone membranes, disclosed in U.S. patent applications Ser. No. 130,566, filed Mar. 4, 1980, now abandoned, and U.S.

Pat. No. 4,629,563, issued Dec. 16, 1986, the disclosures of which are incorporated herein by reference, characterizable as reticular, highly assymetric, having exceptionally good permeability and unusually low resistance to flow for a given pore size. In addition, these preferred supports have unusually smooth and regular skin surfaces, and high pore densities and are thus near ideal support structures for the ultraporous thin film semipermeable membranes of the present invention.

It is also appropriate to select support structures with a view to the physical demands of the intended use and the needs and requirements of the ultraporous thin film semipermeable membranes to be supported. It is important, for example, that the support afford a smooth supporting surface, free of large expanses which require the ultraporous thin film semipermeable membranes to bridge large pores or other artifacts on the support surface. This requirement will ordinarily dictate that the support be skinned, and preferably that it have a very smooth skin. The pores of the support skin are preferably, on the order of about 0.1 to 0.5, more preferably from about 0.1 to 0.2 microns in diameter. Larger pores impose great physical burdens on the ultraporous thin film semipermeable membranes by the requirement that the large spans across the pores are preferably self supporting, and therefore the span is preferably no larger than necessary. Smaller pores, below about 0.1 micron, are generally undesirable since they then would tend to contribute to limiting porosity of the composite, and retard flow rates through the composite to a degree to be avoided if possible.

Given the dimensions of the thin films in the present invention, while they are a material advance in physical integrity and strength in comparison with the prior art thin films, they are, nonetheless, relatively fragile structures in an absolute sense. For many polymer systems, the integrity of the thin film can be greatly enhanced by the provision of a gel layer to aid in bridging the pores of the support. Particularly for monomolecular thin films, it is noteworthy that a film which is 0.0015 microns thick may be required to bridge a pore diameter of 0.1 microns or more. It is readily apparent that when the thickness of the film is on the order of only 1.5% of the span, the physical demands are considerable.

In that context, it is apparent that the provision of an intermediate support gel layer, which forms an intermediate supporting structure, can be of considerable assistance in improving the physical support for the support surface thin film membrane layer.

In another context, some microporous support layers have limited pore densities on the surface, and when the support surface thin film membrane is in direct adherent contact with the surface, only those areas of the support surface thin film membrane which directly overlie the pore area are able to function; the other areas of the support surface thin film membrane will be blocked by the dense surface of the support. In that eventuality, an intermediate support gel layer will provide a flow path from such "blocked" areas of the support surface thin film membrane to an adjacent pore of the support.

When such intermediate support gel layers are employed, it is desirable that the thickness of the layer, in hydrated form be sufficient to afford the physical parameters required, and no more. While this will be very much greater than the dimensions of the support surface thin film membrane, it will ordinarily be on the order of about 0.1 to 5, and preferably about 0.5 to 2, microns in the gel state, less in the event the gel is dried. Thinner intermediate support gel layers introduce the risk of the gel layer being discontinuous, while thicker layers unacceptably increase the resistance to flow and diffusion.

The specific demands of the environment of use will ordinarily dictate the particular requirements of the intermediate support gel layer. When used in an aqueous environment the intermediate support gel will necessarily be a hydrogel. The polymer employed is preferably gel forming in the media with which it will be used. The gel preferably has a porosity greater than that of the ultraporous support surface thin film membranes with which it is employed. It preferably resists degradation and attack in the context of use. It preferably has adequate resistance to pressure to avoid excessive compression or compaction in use at the pressure differentials needed for the service. It preferably does not have components soluble in the context of use which could contaminate the media being processed, and preferably does not interact in any impermissible way with the process stream in use.

It is central to the present invention, however, that the techniques of interfacial condensation are not, as is usual in the membrane art, permitted to proceed to a fully cross linked state in order to provide a thin film membrane. By one or more of the techniques discussed herein, the procedure is modified to produce ultraporous thin film membranes by virtue of control of the cross link density in the resulting thin film, through regulating the determinants of cross link formation.

Cross link density is, in the context of the present invention, the level of cross linking appropriate to produce pores in the ultraporous thin film membranes of the desired size. The desired pore size will vary depending on the enzyme used in the reactor. The size of the pores is preferably small enough to prevent the enzymes and coenzyme from passing through the pores yet large enough to allow for the best possible flow rate of substrate and product through the ultraporous thin film membrane. Of course, in the case where the coenzyme is the same size as or smaller than the substrate or product molecules, the coenzyme can be retained in the hydrogel layer in this situation by using solvents for the substrates and other products in which the coenzyme is insoluble.

It is a part of the present invention to provide techniques for the control of cross link density in the thin films to assure that the required limiting pore sizes in the ultraporous range in relation to the desired substrate and reaction product are attained. The techniques disclosed and claimed in Wrasidlo, ULTRAFILTRATION THIN FILM MEMBRANES, U.S. Pat. No. 4,956,289 are incorporated herein by reference.

With the selection of appropriate materials and pore sizes, the ultraporous thin film semipermeable membranes or the ultraporous support surface thin film membranes of the present invention are particularly desirable for use in molecular separations in the embodiment of the present invention using two thin film membranes, where particular advantage can be taken of the low flow resistance as well as the relative freedom from plugging and fouling to permit the separate recovery of the product through diffusion through the support surface thin film membrane and through the support into a product stream which remains free of the substrate. A molecular separation occurs at the support surface thin film membrane, driven by the concentration gradient of the product between the hydrogel and the product stream. In this circumstance, the structure is best achieved by the employment of one of the supported thin film membrane composites disclosed and claimed in Wrasidlo, ULTRAFILTRATION THIN FILM MEMBRANES, Ser. No. 920,365. The enzyme hydrogel is applied directly on the surface of the support surface thin film membrane, and the feed stream diffusion barrier is another thin film membrane formed, preferably in situ, on the surface of the enzyme hydrogel. In this context, the support may contain an integral intermediate support gel layer as a part of its structure or if appropriate, the intermediate support gel layer may be omitted.

For those enzyme-substrate reactions which result in cleavage of the substrate molecule, as in the case of lysis reactions in general, as well as others, it is often the case that the product molecule or molecules are smaller than the feed substrate molecule in their effective molecular diameter. When such conditions are present, it will often be possible and even preferred to use the alternate embodiment of the present invention wherein the support is a porous diffusion barrier itself. As already discussed, the preferred support for this embodiment is, in any such case, a composite ultraporous thin film membrane on a microporous support. The reactor vessel in that case will be more complex, as shown schematically in FIG. 3. It is necessary to establish plural streams, of substrate feed and effluent, and additionally a product stream feed and effluent. In operation, the substrate feed, rich in substrate for both the coenzyme-requiring enzyme and the regeneration enzyme, is pumped into the vessel, following a flow path along the feed diffusion barrier surface, and the stream, depleted in substrate then passes out of the vessel. As previously discussed, the substrate molecules diffuse from the high concentration feed stream through the thin film semipermeable membrane, into the relatively low concentration enzyme hydrogel reaction zone, where the reactions between substrates and enzymes occur. While, initially, the products formed, exclusive of the coenzyme, will diffuse into the low concentration substrate stream, the level builds until an equilibrium level of concentration is established, and lacking a concentration gradient, no net diffusion of the reaction product into the substrate feed occurs once that condition is established. In a second flow path, in diffusive contact with the porous support, there is established a flow of solvent for the products of both the reactions, exclusive of the coenzyme, maintained with a low concentration of the reaction products. Thus a substantial concentration gradient is established between the products in the enzyme hydrogel reaction zone and the product flow stream, and diffusion of the products through the support surface thin film membrane will occur. The high permeability of the microporous support layer aids in facilitating the product diffusion, although it is preferable that the microporous support be as thin as possible, since the distance over which the diffusion occurs is a factor in the production rate of the system. The products are continuously recovered from the product effluent stream. With appropriate selection of pore sizes in the diffusion barrier layers, none of the substrate will diffuse into the product stream, and the product recovery and purification will be greatly facilitated. The capacity of the present system to perform and sustain such a molecular separation of substrate and product is a major advantage of the low incidence of plugging and fouling of the thin film ultraporous diffusion barriers employed in the present invention.

Figure 4:
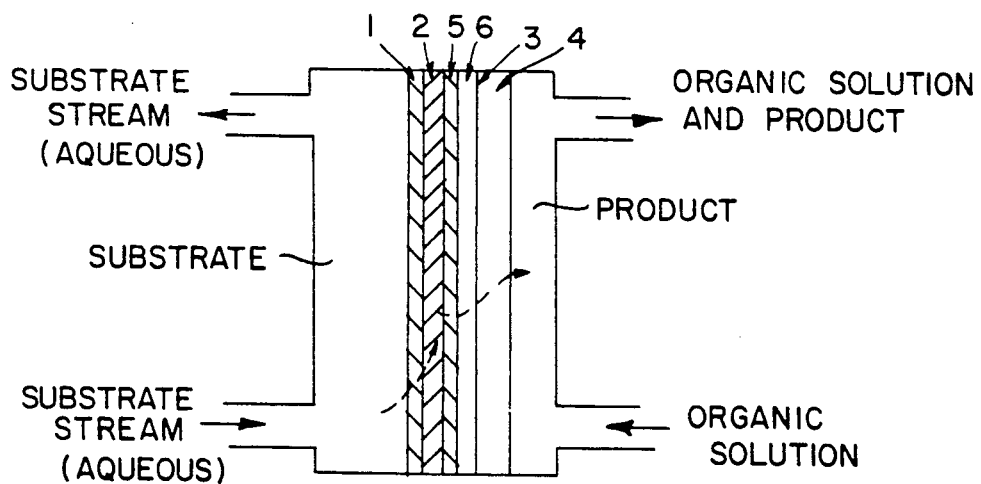
FIG. 4 shows a schematic reaction flow diagram, showing the operation of the invention in its extraction embodiment and yet another embodiment of the structure of the ultraporous thin film membrane enzyme reactor of the present invention.

Variations of this flow through embodiment of the enzyme reactor are possible. For example, non-aqueous solvents such as hexane or toluene may be used as the product feed and effluent. This variant, as shown schematically in FIG. 4, allows for the extraction of product in cases where the substrate is insoluble or nearly so in the non-aqueous solvent, or not able to pass through the support thin film, or otherwise not able to get into the product extract. The enzyme reactor shown in this embodiment is similar to that shown in FIG. 3. The support 4 is porous, preferably microporous, and has interposed between its surface 3 and the enzyme hydrogel 2 the support surface thin film membrane 5. As in the simplest embodiment of the invention, the thin film diffusion barrier 1 is supported on and confines enzyme hydrogel layer 2. In this embodiment, there is found between the support surface thin film membrane 5 and the support surface 3 a thin, freely porous gel layer, the intermediate support gel layer 6. The components of this embodiment are described in more detail above, in connection with the description of the embodiment shown in FIG. 3.

The opposite variation, using a non-aqueous substrate feed and effluent and an aqueous product feed and effluent, is also useful in certain situations. It is also theoretically possible to have both the substrate feed and effluent and the product feed and effluent be non-aqueous solvents. This would be effective where the coenzyme is the same size as or smaller than the substrate or product molecules. This would also be effective where the substrate is highly soluble in the enzyme hydrogel inside the thin film semipermeable membrane, and the product is not. In this case, the product would be less likely to diffuse back into the enzyme hydrogel layer. If appropriate solvents were chosen, the substrate would not likely diffuse through the support into the non-aqueous product solvent. Although this variation, using various combinations of aqueous and non-aqueous solvents, is similar to an extraction, the actual transport of the substrate and product along the thin film membranes will be different from a liquid-liquid extraction.

In practice, the reactor vessel will be packed with a large number of the plate and separator elements, maximizing for the construction employed the diffusion surface areas of the composite elements, and thus maximizing the reactor through-put capacity and productive capacity. The structural concept shown schematically in the figures can readily be adapted by those of ordinary skill to a wide variety of reaction vessels, including plate and frame reactors, tube and manifold reactors, spiral wound cartridge configurations, and the like.

As those of ordinary skill in the art will appreciate, one of the greatest benefits of the present system is that the coenzyme-requiring enzyme, coenzyme, and regeneration enzyme act in their unaltered forms, and will react in a highly predictable fashion to all the usual and customary parameters employed to control enzyme catalyzed reactions. Among these are the control of pH, temperature, pressure, ionic strength, electrical charges, and a variety of activating and inhibiting constituents, such as metal ion activators, cofactors and coenzymes, stabilizers, and competitive and irreversible inhibitors, substrate concentration, product accumulation and the like. These parameters of enzymatic reactions are well known. It is important to note that any factor which is needed in the reaction zone is preferably either available from the feed by diffusion, or incorporated into the hydrogel at the time of its formation if it cannot diffuse through the thin film semipermeable membrane.

EXAMPLES

EXAMPLE 1

A common, loosely bound coenzyme in nearly all life forms is nicotinamide adenine dinucleotide, NAD(P), which is found in both the phosphorylated (NADP) and unphosphorylated (NAD) forms, depending upon the location and function within the cell. The B vitamin, niacin, which is an essential nutrient in humans, is a substrate for the production of NAD(P) which effects enzymic oxidations and reductions. When NAD(P) is used as a coenzyme, depending on whether oxidizing or reducing power is needed, the reaction is either, NAD(P)+substrate-H NAD(P)H+substrate (oxidation), or, NAD(P)H+substrate NAD(P)+substrate-H(reduction).

An example of such an enzyme system would be the use of an NAD-dependent alcohol dehydrogenase to convert an alcohol into an aldehyde. An alcohol when oxidized becomes an aldehyde, while NAD(P) is reduced to NAD(P)H. The alcohol loses two hydrogens in the reaction. One NAD molecule will be required for each alcohol molecule oxidized. One NADH molecule will be generated for each aldehyde molecule formed. The NAD(P) molecule will pick up one hydrogen atom with two electrons, hence the reducing equivalent, to form NAD(P)H. The other hydrogen will go into solution as the ion $H^+$.

To use a specific example, if Aldehyde I is the desired product of the process, then Alcohol I will be the substrate for the reaction. Alcohol I will be provided in the solvent system at a concentration empirically determined to maximize the reaction rate. Aldehyde I will be carried away by the solvent, the flow rate of which is preferably balanced to provide substrate and remove product. The NAD coenzyme required for the reaction is trapped within the hydrogel layer at a fixed concentration along with the alcohol dehydrogenase necessary to catalyze the conversion of Alcohol I to Aldehyde I. Since there is a finite amount of NAD present within the hydrogel layer of the reactor, as the conversion of Alcohol I into Aldehyde I progresses the concentration of NAD decreases and the concentration of NADH increases. The reaction will come to a rapid halt if an efficient coenzyme regeneration system is not present. To oxidize the NADH formed in the desired reaction, a second dehydrogenase which favors the reverse reaction can be used. With over 200 pyridine-linked dehydrogenases known, proper attention to redox potentials for substrate couples preferably produces a regeneration system for any desired reaction. To insure that the NADH oxidation occurs as rapidly as possible, the substrate Aldehyde II, is provided in the solvent at high concentration. Thus, this aldehyde is preferably relatively cheap, e.g., acetaldehyde. The product of the regeneration reaction will be Alcohol II (in the case of acetaldehyde, ethanol). Alcohol II can only be produced as rapidly as Aldehyde I and will be carried away at the same rate, so is not likely to present any problems regarding inhibition or competition. It may even be possible in some cases to produce a second commercial product from the regeneration reaction.

Manipulation of the substrate concentrations and the solvent flow rate will maximize productivity. The requirements of the system are that the product be easily and efficiently separated from the other components present in the solvent. A wide variety of substrates are available for the regeneration reaction in most cases and choice of appropriate system components is not likely to present few problems. Thus an enzyme with loosely bound, diffusable coenzyme requirements can now be efficiently and economically scaled up to an industrial In vitro process using this modification of the enzyme reactor of Ser. No. 026,380.

EXAMPLE 2

A 10 cm by 10 cm hydrophilic Nylon sheet is coated with an aqueous solution of 5% alcohol dehydrogenase and aromatic alcohol dehydrogenase. After the film has dried to gel consistency, a 0.5% polyethyleneimine (MW 60,000) solution is applied and the resultant wet film drained for 5 minutes in a circulating air environment. The sheet is then immersed for 5 minutes in a solution of 0.1% toluene-diisocyanate in hexane. The thin film-enzyme-composite is rinsed three times with hexane prior to exposure to an aqueous 10 mM NAD solution for 10 minutes. The film can now be exposed to a water saturated toluene stream that is also saturated with the substrates benzylalcohol and butyraldehyde. The products, benzylaldehyde and butylalcohol, can be harvested downstream.

When the reaction rate drops below the desired minimum level the thin film composite can be recharged with coenzyme by a brief exposure to the aqueous NAD solution. Alternatively, the toluene can be saturated with NAD. This would prevent any loss of coenzyme from the composite.

We claim:

1. An enzyme reactor comprising:
   a support;
   an enzyme hydrogel layer on said support, said enzyme hydrogel layer comprising an aqueous gel of a coenzyme-requiring enzyme, a coenzyme for said primary coenzyme-requiring enzyme, and a regeneration enzyme for said coenzyme;
   said coenzyme-requiring enzyme being such as to catalyze a reaction involving a substrate and said coenzyme so as to form a product;
   said regeneration enzyme being such as to catalyze a reaction involving a substrate so as to form a product, said product including said coenzyme; and
   a porous thin film semipermeable membrane on said enzyme hydrogel layer, wherein said thin film semipermeable membrane has a thickness of from about 0.0012 to 0.2 microns and a pore size sufficient to permit diffusion of said substrate for said coenzyme-requiring enzyme, of said product of said reaction catalyzed by said coenzyme-requiring enzyme, of said substrate for said regeneration enzyme, and of said product of said reaction catalyzed by said regeneration enzyme, including said coenzyme; but which does not permit said coenzyme-requiring enzyme, said coenzyme, or said regeneration enzyme to pass through said thin film semipermeable membrane.

2. The reactor of claim 1, wherein said support is impermeable.

3. The reactor of claim 1, wherein said support comprises:
   an impermeable support surface thin film layer in contact with said enzyme hydrogel layer and
   an open porous layer physically supporting said support surface thin film layer.

4. The reactor of claim 1, wherein said support comprises:
   a support surface thin film layer in contact with said enzyme hydrogel layer which is permeable to said substrate for said coenzyme-requiring enzyme, to said product of said reaction of said substrate and said coenzyme-requiring enzyme, to said substrate for said regeneration enzyme, and to said product of said reaction of said substrate for said regeneration enzyme catalyzed by said regeneration enzyme, but which will not permit said coenzyme-requiring enzyme, said coenzyme, or said regeneration enzyme to pass through said support surface layer, and
   an open porous layer physically supporting said support surface thin film layer.

5. The reactor of claim 4, wherein there is interposed between said support surface thin film layer and said open porous layer physically supporting said support surface thin film layer a thin, gel layer that is freely permeable to said substrates and said products.

6. The reactor of claim 1, wherein said support comprises:
   a support surface thin film layer in contact with said enzyme hydrogel layer which is permeable to said product of said reaction of said substrate for said coenzyme-requiring enzyme and said coenzyme-requiring enzyme and to said product of said reaction of said substrate for said regeneration enzyme and said regeneration enzyme, but which will not permit said substrate for said coenzyme-requiring enzyme, said substrate for said regeneration enzyme, said coenzyme-requiring enzyme, said coenzyme, or said regeneration enzyme to pass through said support surface layer, and
   an open porous layer physically supporting said support surface thin film layer.

7. The reactor of claim 6, wherein there is interposed between said support surface thin film layer and said open porous layer physically supporting said support surface thin film layer a thin gel layer that is freely permeable to said substrates and said products.

8. The reactor of claim 1, wherein said support is a dense support having a high surface area per unit volume.

9. The reactor of claim 1, wherein said enzyme hydrogel layer further comprises a hydrogel forming polymer.

10. The reactor of claim 9, wherein said hydrogel forming polymer is cross linked.

11. The reactor of claim 9, wherein said hydrogel forming polymer is irreversibly bound to said support and to said thin film membrane.

12. The reactor of claim 9, wherein said coenzyme-requiring enzyme, said coenzyme, and said regeneration enzyme are physically entrapped in said hydrogel forming polymer in an amount of from about 10 to about 90 weight percent of said hydrogel forming polymer, on a solids basis.

13. A method of using an enzyme reactor comprising the steps of:
    forming an enzyme reactor which comprises
    a support;
    an enzyme hydrogel layer on said support, said enzyme hydrogel layer comprising an aqueous gel of a coenzyme-requiring enzyme, a coenzyme for said primary coenzyme-requiring enzyme, and a regeneration enzyme for said coenzyme; and
    a porous thin film semipermeable membrane on said enzyme hydrogel layer;
    placing said enzyme reactor into a reactor vessel;
    dissolving a substrate for said coenzyme-requiring enzyme in a solvent therefor;
    dissolving a substrate for said regeneration enzyme in a solvent therefor;
    passing said dissolved substrate for said coenzyme-requiring enzyme and said dissolved substrate for said regeneration enzyme through said reactor vessel in such a manner that said substrate for said coenzyme-requiring enzyme and said substrate for said regeneration enzyme and said solvent therefor are in contact with said porous thin film diffusion membrane;
    allowing said substrate for said coenzyme-requiring enzyme to react with said coenzyme-requiring enzyme, thereby forming a product of said reaction catalyzed by said coenzyme-requiring enzyme and allowing said substrate for said regeneration enzyme to react with said regeneration enzyme, thereby forming a product of said reaction catalyzed by said regeneration enzyme; and
    collecting the product of said reaction catalyzed by said coenzyme-requiring enzyme and the product of said reaction catalyzed by said regeneration enzyme, exclusive of said coenzyme.

14. The method of claim 13, wherein said substrate for said coenzyme-requiring enzyme and said substrate for said regeneration enzyme diffuse through said thin film semipermeable membrane and into said enzyme hydrogel layer prior to reacting with said coenzyme-requiring enzyme, said coenzyme, and said regeneration enzyme.

15. The method of claim 13, wherein said product of said reaction of said substrate for said coenzyme-requiring enzyme and said coenzyme-requiring enzyme and the product of said reaction of said substrate for said regeneration enzyme and said regeneration enzyme, exclusive of said coenzyme, are collected by allowing said product of said reaction of said substrate for said coenzyme-requiring enzyme and said coenzyme-requiring enzyme and the product of said reaction of said substrate for said regeneration enzyme and said regeneration enzyme, exclusive of said coenzyme, to diffuse from said enzyme hydrogel layer through said thin film semipermeable membrane and into said solvent for said substrate for said coenzyme-requiring enzyme and said substrate for said regeneration enzyme.

16. The method of claim 13, wherein said hydrogel layer further comprises a hydrogel forming polymer.

17. The method of claim 13, wherein said support further comprises:
    a support surface thin film layer in contact with said enzyme hydrogel layer which is permeable to said substrate for said coenzyme-requiring enzyme, to said product of said reaction of said substrate and said coenzyme-requiring enzyme, to said substrate for said regeneration enzyme, and of said product of said reaction of said substrate for said regeneration enzyme catalyzed by said regeneration enzyme, exclusive of said coenzyme, but which does not permit said coenzyme-requiring enzyme, said coenzyme, or said regeneration enzyme to pass through said support surface layer, and an open porous layer physically supporting said support surface thin film layer.

18. The method of claim 17, wherein said substrate for said coenzyme-requiring enzyme and said substrate for said regeneration enzyme diffuse through said thin film semipermeable membrane and into said enzyme hydrogel layer prior to reacting with said coenzyme-requiring enzyme, said coenzyme, and said regeneration enzyme.

19. The method of claim 17, wherein there is a solvent for said product of said reaction of said substrate for said coenzyme-requiring enzyme and said coenzyme-requiring enzyme and the product of said reaction of said substrate for said regeneration enzyme and said regeneration enzyme which is in contact with the surface of said open porous layer of said support which is not in contact with said support surface thin film layer.

20. The method of claim 19, wherein said product of said reaction of said substrate for said coenzyme-requiring enzyme and said coenzyme-requiring enzyme and the product of said reaction of said substrate for said regeneration enzyme and said regeneration enzyme, exclusive of said coenzyme, diffuse through said support surface thin film layer and said open porous layer of said support into said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

21. The method of claim 19, wherein said substrate for said coenzyme-requiring enzyme and said substrate for said regeneration enzyme are soluble in said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

22. The method of claim 19, wherein said substrate for said coenzyme-requiring enzyme and said substrate for said regeneration enzyme are insoluble in said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

23. The method of claim 19, wherein said product of said reaction of said substrate for said coenzyme-requiring enzyme and said coenzyme-requiring enzyme and the product of said reaction of said substrate for said regeneration enzyme and said regeneration enzyme, exclusive of said coenzyme, are insoluble in said solvent for said substrate for said coenzyme-requiring enzyme and said substrate for said regeneration enzyme.

24. The method of claim 19, wherein there is interposed between said support surface thin film layer and said open porous layer physically supporting said support surface thin film layer a thin, gel layer that is freely permeable to said substrate and said products.

25. The method of claim 24, wherein there is a solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme, in contact with the surface of said open porous layer of said support which is not in contact with said support surface thin film layer.

26. The method of claim 24, wherein said product of said reaction of said substrate for said coenzyme-requiring enzyme and said coenzyme-requiring enzyme and the product of said reaction of said substrate for said regeneration enzyme and said regeneration enzyme, exclusive of said coenzyme, diffuse through said support surface thin film layer and said open porous layer of said support into said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

27. The method of claim 24, wherein said substrate for said coenzyme-requiring enzyme and said substrate for said regeneration enzyme are soluble in said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

28. The method of claim 24, wherein said substrate for said coenzyme-requiring enzyme and said substrate for said regeneration enzyme are insoluble in said solvent for said product of said reaction of said substrate for said coenzyme-requiring enzyme and said coenzyme-requiring enzyme and the product of said reaction of said substrate for said regeneration enzyme and said regeneration enzyme, exclusive of said coenzyme.

29. The method of claim 24, wherein said product of said reaction of said substrate for said coenzyme-requiring enzyme and said coenzyme-requiring enzyme and the product of said reaction of said substrate for said regeneration enzyme and said regeneration enzyme, exclusive of said coenzyme, are insoluble in said solvent for said substrate for said coenzyme-requiring enzyme and said substrate for said regeneration enzyme.

* * * * *